US006283988B1

(12) United States Patent
Laufer et al.

(10) Patent No.: US 6,283,988 B1
(45) Date of Patent: *Sep. 4, 2001

(54) BRONCHIAL STENTER HAVING EXPANDABLE ELECTRODES

(75) Inventors: Michael D. Laufer, Menlo Park; Keith M. Burger, San Francisco; Bryan E. Loomas, Saratoga; Don A. Tanaka, San Jose, all of CA (US)

(73) Assignee: Broncus Technologies, Inc., Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/260,401

(22) Filed: Mar. 1, 1999

Related U.S. Application Data (63) Continuation-in-part of application No. 09/003,750, filed on Jan. 7, 1998, now Pat. No. 5,972,026, and a continuation-in-part of application No. 08/833,550, filed on Apr. 7, 1997.

(51) Int. Cl.[7] .................................................... A61F 2/00
(52) U.S. Cl. ............................ 607/96; 607/101; 607/105; 607/115
(58) Field of Search .............................. 607/96, 101, 102, 607/113; 606/41, 45–47, 49–50

(56) References Cited

U.S. PATENT DOCUMENTS

| 3,667,476 | 6/1972 | Muller . |
| 3,995,617 | 12/1976 | Watkins et al. . |
| 4,116,589 | 9/1978 | Rishton . |
| 4,129,129 | 12/1978 | Amrine . |
| 4,502,490 | 3/1985 | Evans et al. . |
| 4,522,212 | 6/1985 | Gelinas et al. . |

(List continued on next page.)

FOREIGN PATENT DOCUMENTS

| 280 225 A2 | 8/1988 | (EP) . |
| 286 145 A2 | 10/1988 | (EP) . |
| 286 145 A3 | 10/1988 | (EP) . |
| 768 091 A1 | 4/1997 | (EP) . |
| 2 233 293 | 1/1991 | (GB) . |
| 545 358 | 7/1977 | (RU) . |
| WO 97/40751 | 11/1997 | (WO) . |
| WO 99/03413 | 1/1999 | (WO) . |

OTHER PUBLICATIONS

Kitamura, S., Color Atlas of Clinical Application of Fiberoptic Bronchoscopy, p. 17, (Mosby–Year Book, Inc., 1990).

*Primary Examiner*—Lee Cohen
*Assistant Examiner*—Roy Gibson
(74) *Attorney, Agent, or Firm*—Morrison & Foerster LLP (57) ABSTRACT

An apparatus and method are provided for treating collapsed bronchial tubes found in patients with chronic obstructive pulmonary diseases, such as asthma. The apparatus delivers energy to inductively heat the tissue of the bronchial tube by directing electromagnetic energy into the tissue. The apparatus includes expandable electrodes that come into contact with the walls of the bronchial tubes. The expandable electrodes may be conical-shaped electrodes, loop-shaped electrodes, plate-shaped electrodes, or other shapes. The method includes heating the bronchial tube to cause tissue in the wall of the bronchial tube to undergo a structural transformation effective to render the wall capable of supporting a non-collapsed lumen. The procedure effectively reinforces the structural integrity of the bronchial tube wall and thereby prevents the lumen from collapsing.

28 Claims, 5 Drawing Sheets

U.S. PATENT DOCUMENTS

| | | |
|---|---|---|
| 4,557,272 | 12/1985 | Carr . |
| 4,567,882 | 2/1986 | Heller . |
| 4,584,998 | 4/1986 | McGrail . |
| 4,621,882 | 11/1986 | Krumme . |
| 4,625,712 | 12/1986 | Wampler . |
| 4,646,737 | 3/1987 | Hussein et al. . |
| 4,674,497 | 6/1987 | Ogasawara . |
| 4,683,890 | 8/1987 | Hewson . |
| 4,704,121 | 11/1987 | Moise . |
| 4,709,698 | 12/1987 | Johnston et al. . |
| 4,772,112 | 9/1988 | Zider et al. . |
| 4,779,614 | 10/1988 | Moise . |
| 4,802,492 | 2/1989 | Grunstein . |
| 4,817,586 | 4/1989 | Wampler . |
| 4,825,871 | 5/1989 | Cansell . |
| 4,846,152 | 7/1989 | Wampler et al. . |
| 4,895,557 | 1/1990 | Moise et al. . |
| 4,906,229 | 3/1990 | Wampler . |
| 4,908,012 | 3/1990 | Moise et al. . |
| 4,920,978 | 5/1990 | Colvin . |
| 4,944,722 | 7/1990 | Carriker et al. . |
| 4,955,377 | 9/1990 | Lennox et al. . |
| 4,969,865 | 11/1990 | Hwang et al. . |
| 4,976,709 | 12/1990 | Sand . |
| 4,985,014 | 1/1991 | Orejola . |
| 4,991,603 | 2/1991 | Cohen et al. . |
| 5,009,636 | 4/1991 | Wortley et al. . |
| 5,019,075 | 5/1991 | Spears et al. . |
| 5,036,848 | 8/1991 | Hewson . |
| 5,053,033 | 10/1991 | Clarke . |
| 5,084,044 | 1/1992 | Quint . |
| 5,096,916 | 3/1992 | Skupin . |
| 5,103,804 | 4/1992 | Abele et al. . |
| 5,105,826 | 4/1992 | Smits et al. . |
| 5,117,828 | 6/1992 | Metzger et al. . |
| 5,167,223 | 12/1992 | Koros et al. . |
| 5,191,883 | 3/1993 | Lennox et al. . |
| 5,213,576 | 5/1993 | Abiuso et al. . |
| 5,231,996 | 8/1993 | Bardy et al. . |
| 5,232,444 | 8/1993 | Just et al. . |
| 5,234,456 | 8/1993 | Silvestrini . |
| 5,255,678 | 10/1993 | Deslauriers et al. . |
| 5,255,679 | 10/1993 | Imran . |
| 5,269,758 | 12/1993 | Taheri . |
| 5,293,869 | 3/1994 | Edwards et al. . |
| 5,309,910 | 5/1994 | Edwards et al. . |
| 5,313,943 | 5/1994 | Houser et al. . |
| 5,345,936 | 9/1994 | Pomeranz et al. . |
| 5,368,591 | 11/1994 | Lennox et al. . |
| 5,374,287 | 12/1994 | Rubin . |
| 5,393,207 | 2/1995 | Maher et al. . |
| 5,400,778 | 3/1995 | Jonson et al. . |
| 5,415,166 | 5/1995 | Imran . |
| 5,423,811 | 6/1995 | Imran et al. . |
| 5,433,730 | 7/1995 | Alt . |
| 5,437,665 * | 8/1995 | Munro ..................................... 606/47 |
| 5,443,470 | 8/1995 | Stern et al. . |
| 5,456,667 | 10/1995 | Ham et al. . |
| 5,458,596 | 10/1995 | Lax et al. . |
| 5,465,717 | 11/1995 | Imran et al. . |
| 5,471,982 | 12/1995 | Edwards et al. . |
| 5,478,309 | 12/1995 | Sweezer et al. . |
| 5,496,311 | 3/1996 | Abele et al. . |
| 5,509,419 | 4/1996 | Edwards et al. . |
| 5,545,161 | 8/1996 | Imran . |
| 5,545,193 | 8/1996 | Fleischman et al. . |
| 5,549,559 | 8/1996 | Eshel . |
| 5,562,608 | 10/1996 | Sekins et al. . |
| 5,571,074 | 11/1996 | Buckman, Jr. et al. . |
| 5,578,072 | 11/1996 | Barone et al. . |
| 5,588,432 | 12/1996 | Crowley . |
| 5,588,812 | 12/1996 | Taylor et al. . |
| 5,595,183 | 1/1997 | Swanson et al. . |
| 5,601,088 | 2/1997 | Swanson et al. . |
| 5,605,157 | 2/1997 | Panescu et al. . |
| 5,607,462 | 3/1997 | Imran . |
| 5,630,425 | 5/1997 | Panescu et al. . |
| 5,641,326 | 6/1997 | Adams . |
| 5,680,860 | 10/1997 | Imran . |
| 5,681,308 | 10/1997 | Edwards et al. . |
| 5,695,471 | 12/1997 | Wampler . |
| 5,707,218 | 1/1998 | Maher et al. . |
| 5,707,336 | 1/1998 | Rubin . |
| 5,707,352 | 1/1998 | Sekins et al. . |
| 5,722,401 | 3/1998 | Pietroski et al. . |
| 5,722,403 | 3/1998 | McGee et al. . |
| 5,722,416 | 3/1998 | Swanson et al. . |
| 5,727,569 | 3/1998 | Benetti et al. . |
| 5,730,741 | 3/1998 | Horzewski et al. . |
| 5,740,808 | 4/1998 | Panescu et al. . |
| 5,752,518 | 5/1998 | McGee et al. . |
| 5,755,714 | 5/1998 | Murphy-Chuthorian . |
| 5,755,753 | 5/1998 | Knowlton . |
| 5,759,158 | 6/1998 | Swanson . |
| 5,765,568 | 6/1998 | Sweezer, Jr. et al. . |
| 5,769,846 | 6/1998 | Edwards et al. . |
| 5,779,698 * | 7/1998 | Clayman et al. ..................... 606/39 |
| 5,782,797 | 7/1998 | Schweich, Jr. et al. . |
| 5,782,848 | 7/1998 | Lennox . |
| 5,782,899 | 7/1998 | Imran . |
| 5,792,064 | 8/1998 | Panescu et al. . |
| 5,795,303 | 8/1998 | Swanson et al. . |
| 5,800,375 | 9/1998 | Sweezer et al. . |
| 5,807,306 | 9/1998 | Shapland et al. . |
| 5,810,757 | 9/1998 | Sweezer, Jr. et al. . |
| 5,820,554 | 10/1998 | Davis et al. . |
| 5,827,277 | 10/1998 | Edwards . |
| 5,833,651 | 11/1998 | Donovan et al. . |
| 5,836,947 * | 11/1998 | Fleischman et al. ................. 606/47 |
| 5,843,075 | 12/1998 | Taylor . |
| 5,848,969 | 12/1998 | Panescu et al. . |
| 5,855,577 | 1/1999 | Murphy-Chuthorian et al. . |
| 5,860,974 | 1/1999 | Abele . |
| 5,865,791 | 2/1999 | Whayne et al. . |
| 5,871,443 | 2/1999 | Edwards et al. . |
| 5,873,865 | 2/1999 | Horzewski et al. . |
| 5,881,727 | 3/1999 | Edwards . |
| 5,882,346 | 3/1999 | Pomeranz et al. . |
| 5,904,651 | 5/1999 | Swanson . |
| 5,904,711 | 5/1999 | Flom et al. . |
| 5,908,445 | 6/1999 | Whayne et al. . |
| 5,908,446 | 6/1999 | Imran . |
| 5,919,172 | 7/1999 | Golba, Jr. . |
| 5,954,661 | 9/1999 | Greenspon et al. . |
| 5,954,662 | 9/1999 | Swanson et al. . |
| 5,964,753 | 10/1999 | Edwards . |
| 5,964,796 | 10/1999 | Imran . |
| 5,971,983 | 10/1999 | Lesh . |
| 5,984,917 | 11/1999 | Fleischman et al. . |
| 5,991,650 | 11/1999 | Swanson et al. . |
| 5,992,419 | 11/1999 | Sterzer et al. . |
| 5,993,462 | 11/1999 | Pomeranz et al. . |
| 6,004,269 | 12/1999 | Crowley et al. . |
| 6,016,437 * | 1/2000 | Tu et al. ............................ 600/374 |
| 6,024,740 | 2/2000 | Lesh et al. . |
| 6,036,687 | 3/2000 | Laufer et al. . |

\* cited by examiner

BRONCHIAL STENTER HAVING EXPANDABLE ELECTRODES

REFERENCE TO RELATED APPLICATION

This is a continuation-in-part application of U.S. application Ser. No. 08/833,550 filed on Apr. 7, 1997 and U.S. application Ser. No. 09/003,750 filed on Jan. 7, 1998, now U.S. Pat. No. 5,972,026 issued on Oct. 26, 1999.

FIELD OF THE INVENTION

The present invention relates to a device and method for treatment of the airway obstruction found in chronic obstructive pulmonary diseases (COPD), such as cystic fibrosis, chronic bronchitis, emphysema, and asthma.

BACKGROUND OF THE INVENTION

Chronic obstructive pulmonary diseases (COPD), which include such entities as cystic fibrosis, chronic bronchitis, emphysema, and asthma are steadily increasing in frequency, possibly due to continued smoking, increasing air pollution, and the continued aging of the population. COPD is characterized by edema of the mucous membranes, which line the interior walls of the tracheobronchial tree. When the mucosa accumulates an abnormal quantity of liquid, the profuse and thickened serous fluid excreted may seriously affect ventilation in the alveoli. The mucus resists movement up the walls of the tracheobronchial tree, normally efficiently accomplished by the cilia throughout the airways which are also destroyed. Consequently, the serous fluid can form mucus plugs, which can shut off alveoli or entire airways. In addition to secretion accumulation, airway obstruction can occur because the tubes collapse due to destruction of connective tissue. This reduces the ability to get oxygen into the blood and carbon dioxide out of the blood.

Asthma is the most common form of bronchoconstrictive disease and pathologically involves constriction of the bronchioles, hypertrophy of the muscles of the bronchioles, and a characteristic infiltrate of eosinophils. Both asthma and other COPDs are characterized by the constriction or collapse of airway passages in the lungs that are not supported by cartilage. This condition is marked by labored breathing accompanied by wheezing, by a sense of constriction in the chest, and often by attacks of coughing and gasping. Individuals who are afflicted may attempt to compensate by blowing harder only to have the airways collapse further. A person with poor resulting ventilation suffers from a number of metabolic conditions including accumulation of carbon dioxide. These individuals also often have hyperinflated enlarged lungs and barrel-shaped chests.

A wide variety of drugs are available for treating the symptoms of COPD but none is curative. Cystic fibrosis, chronic bronchitis, and emphysema are typically treated with agents to thin and dry up the secretions and with antibiotics to combat infection and with bronchodilators. These drugs include potassium iodide, antihistamines, various antibiotics, beta agonists, and aminophylline. Unfortunately, a large number of patients are not responsive to these medications or become non-responsive after prolonged periods of treatment. For severe cases involving collapsed air passages, surgeons have endeavored to alleviate this disabling condition by either removing a portion of the lungs or constricting the volume of lung available for respiration by stapling off sections thereof. The result is that functionally the diaphragm and muscles in the chest wall operate on a smaller lung volume which may improve air movement for some individuals. These operations are quite risky and are associated with a large number of deaths. Patients undergoing these treatments are quite ill and these procedures are considered final options.

Notwithstanding the conventional treatments available, there exists a need in the art for an effective treatment for chronic obstructive pulmonary diseases, such as cystic fibrosis, chronic bronchitis, emphysema, and asthma. Specifically, there is a need for effective treatment for individuals with obstructed airway passages to restore pulmonary function which only requires minimal surgery.

SUMMARY OF THE INVENTION

Many types of tissue can be molded and remodeled to correct defects and dysfunction. One technique involves physical manipulation using mechanical instruments and/or balloons to effect selective shrinking, stretching, flattening, thinning, or thickening in addition to changing the material properties of the tissue. These changes of properties include alteration of the elastic coefficient of the tissue causing it to be stiffer, changing the tensile strength of the tissue, changing the shear strength of the tissue, and changing the floppiness or resiliency of the tissue. When the tissue is close to the surface of the skin or part of a non-critical organ, physical manipulation is feasible and can be executed with minimal trauma to the patient. However, when the tissue is in an internal organ, in particular, in the lungs or other vital organ, molding and remodeling by physical manipulation can involve complicated and often risky surgery.

The present invention is based, in part, on the development of a heat treatment apparatus having expandable electrodes that are capable of delivering energy to bronchial tubes uniformly. The heat is preferably inductively applied by directing electromagnetic energy, such as radio frequency, into the tissue to keep the bronchial tubes open.

In accordance with one aspect of the present invention, a method for treating a bronchial tube includes the steps of:

a) maneuvering a heating apparatus into a lumen of the bronchial tube;

b) heating tissue of the bronchial tube to cause tissue in a wall of the lumen to undergo a structural transformation effective to render the wall capable of supporting the lumen without collapsing; and c) removing the apparatus from the bronchial tube.

Prior to treatment, the lumen can be non-collapsed, partially, or fully collapsed. Preferably, the bronchial tube is heated to a temperature in the range of about 60° C. to about 95° C. for about 0.1 to about 600 seconds. With the inventive procedure, extensive surgery and the accompanying trauma are avoided.

This invention is particularly useful for treating subjects experiencing difficulty in breathing as a result of obstructed airway passages caused by, for example, chronic obstructive pulmonary disease, including, for example, cystic fibrosis, chronic bronchitis, emphysema, and asthma. This invention ameliorates the affects of these diseases by improving lung function by keeping the airway passages open. Specifically, the present invention provides a device and method for effecting changes in soft tissue in the bronchial tubes or air passages of the lungs which have collapsed. The causes of the collapse may be the destruction of the connective tissue, the disease process, swelling, and/or muscle-dependant constriction. The invention is directed to a treatment process which effectively creates an internal bronchial stent which prevents the air passages from collapsing.

In one aspect, the invention is directed to an apparatus for treating a bronchial tube having a lumen, which includes:

a tubular member having a lumen;

an elongated shaft that is at least partially slidably positioned in the lumen of the tubular member;

at least one electrode supported by the elongated shaft, which when energized causes tissue in the wall of the bronchial tube to undergo a structural transformation effective to render the wall capable of supporting the bronchial tube in a non-collapsed configuration, wherein the at least one electrode is pivotally mounted on the elongated shaft and expandable radially outward to contact the wall of the bronchial tube; and a source of energy electrically connected to the at least one electrode.

In another aspect, the invention is directed to a method of treating a bronchial tube comprising a lumen of an individual that includes the step of:

advancing the above described treatment apparatus into the lumen of the bronchial tube; and activating the treatment device to raise the temperature of the wall to sufficiently effect a structural transformation in the tissue of the wall.

BRIEF DESCRIPTION OF THE DRAWINGS

As used herein, like reference numerals will designate similar elements in the various embodiments of the present invention wherein.

DETAILED DESCRIPTION OF THE PREFERRED EMBODIMENTS

Figure 1:
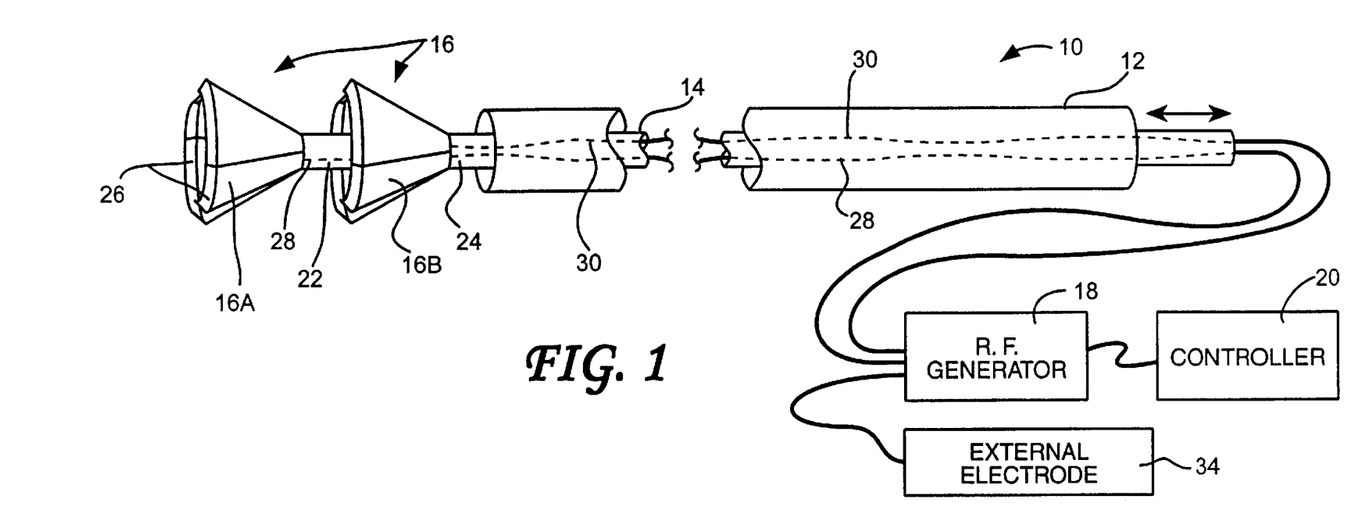
FIG. 1 is a schematic side view of one embodiment of a heat treatment apparatus of the present invention which employs two collapsible and retractable electrodes.

FIG. 1 shows a first embodiment of a heat treatment apparatus 10 which is introduced through a catheter, bronchoscope, or other tubular introducer member 12. The heat treatment apparatus includes a shaft 14 and one or more electrodes 16. Electrically connected to the electrodes 16 is an RF generator 18 or other energy source. The RF generator is controlled by a controller 20. Although the invention will be described as employing an RF generator, other energy sources, such as alternating current and microwave may also be used.

In accordance with the embodiment of FIG. 1, the electrodes include a first conical electrode 16A connected to an inner shaft 22 and a second conical electrode 16B connected to an outer shaft 24. The conical electrodes 16A, 16B are positioned with their axes aligned and may be fixed or movable with respect to each other. Each of the conical electrodes 16A, 16B, includes at least two overlapping sections or opposing portions 26. The sections 26 are flexible and overlap one another to allow the electrodes 16A, 16B to be compressed within the lumen of the catheter 12 for insertion into the bronchial tube of a patient. Once the catheter 12 is positioned with a distal end at a desired treatment location within the bronchial tubes, the shaft 14 is used to push the electrodes 16A, 16B out of the distal end of the catheter. Once deployed from the catheter 12 the electrodes 16A, 16B expand radially outwardly until the distal ends of the electrodes contact the walls of the bronchial tube.

The electrodes 16A, 16B are electrically connected to the RF generator 18 by electrical cables 28, 30. When the heat treatment apparatus 10 employs two electrodes 16A, 16B the two electrodes are preferably oppositely charged with one of the electrodes connected to a negative output of the RF generator and the other electrode connected to a positive output of the RF generator. Alternatively, both the electrodes 16A, 16B or a single electrode 16 may be connected to the same output of the RF generator and an external electrode 34 may be used. The external electrode 34 is connected to an output of the RF generator 18 having an opposite polarity of the output connected to the internal electrode 16.

The present invention is based in part on the discovery that the structural integrity of bronchial tubes, especially those which do not have significant amounts of cartilage present, can be significantly recreated by subjecting the bronchial tubes to a sufficient amount of heat to cause at least a portion of the soft tissue to undergo a structural transformation thereby causing the tubes to remain patent. This structural transformation may be due to a variety of sources such as, scar tissue buildup, collagen restructuring, or the like. This heating procedure changes the structure of the tissue and the shape of the tube.

As used herein, the term "bronchial tube" or "air passage" refers to the sub-segments that branch from the main stem bronchus of the lungs. The term "collapsed lumen" refers to a condition of lumen of a bronchial tube wherein the lumen is occluded to the extent that substantial blockage of air flow through the lumen exists. The diameter of a non-collapsed lumen may be substantially equal to that of a normal bronchial tube or may be less as in the case of a partially collapsed but functional lumen. It is understood that the term "collapsed lumen" encompasses partially collapsed lumens. Cartilage is not present around these air passages in appreciable amounts so they have little intrinsic supportive structures.

Figure 2:
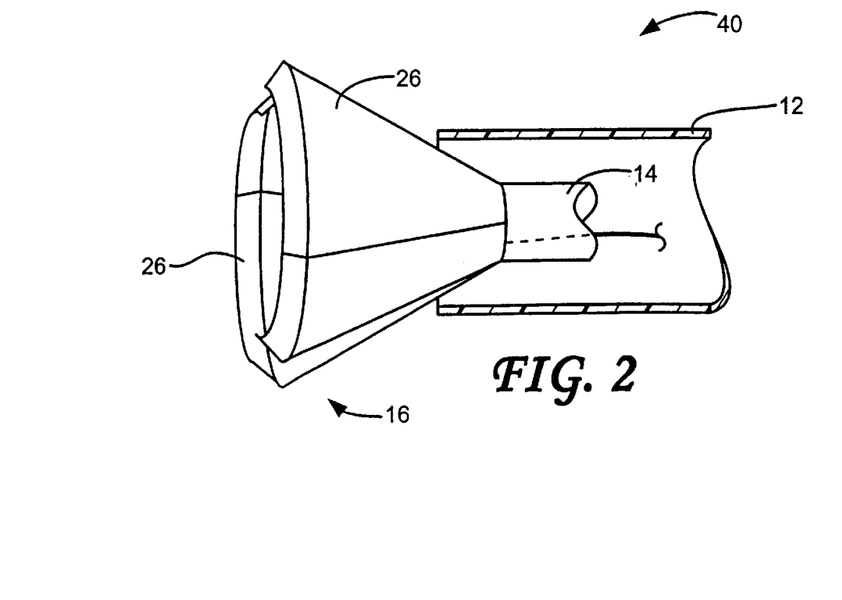
FIG. 2 is an enlarged partial cross sectional view of a distal end of another embodiment of a heat treatment having one collapsible electrode.

FIG. 2 shows an alternative embodiment of a heat treatment apparatus 40 having a single electrode 16 positioned on a shaft 14. The electrode 16 is shown as it is deployed from the distal end of a catheter 12 for heat treatment of the lumen of bronchial tubes.

The electrodes 16 of the embodiment of FIGS. 1 and 2 are formed of a suitable conductive material such as metal, plastic with a metal coating, or the like. The two or more sections 26 of each of the cone shaped electrodes is fixed to the shaft 14 and biased outwardly so that the sections expand or unfold to an enlarged diameter upon release from the distal end of the catheter 12. The electrodes 16 preferably have an enlarged diameter which is equal to or slightly greater than an interior diameter of the bronchial tube to be treated. As shown most clearly in FIG. 2, the sides of the sections 26 overlap one another even in the expanded state.

In operation of the embodiments of FIGS. 1 and 2, the distal end of the catheter 10 is first positioned at the treatment site by known catheter tracking methods. The catheter 10 is then retracted over the heat treatment apparatus to exposed and expand the electrodes 16. Each electrode 16 of the energy emitting apparatus 10 expands radially outward upon retraction of the catheter 12 until the electrodes come into contact with the wall of the bronchial tube. In the embodiment of FIG. 2, the distance between the two energy emitting electrodes 16A, 16B may be fixed or may be changeable by sliding the inner shaft 22 within the outer shaft 24. When treatment is completed the heat treatment apparatus 10 is retracted back inside the catheter 12 by sliding the catheter over the electrodes. As the heat treatment apparatus 10 is retracted the sides of the sections 26 of the electrode 16 slide over each other upon coming into contact with a distal edge of the catheter 12.

Figure 3:
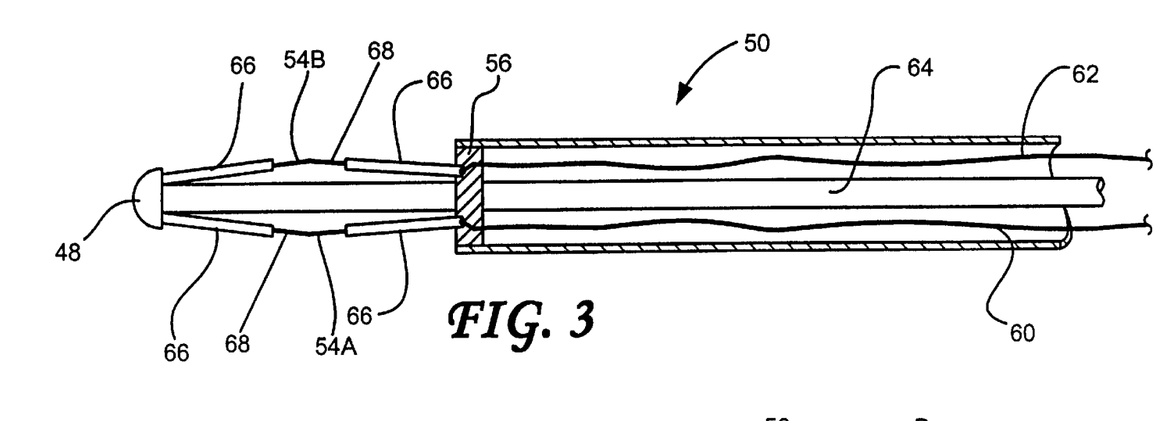
FIG. 3 is a side cross sectional view of an alternative embodiment of a heat treatment device having two wire shape electrodes.
Figure 4:
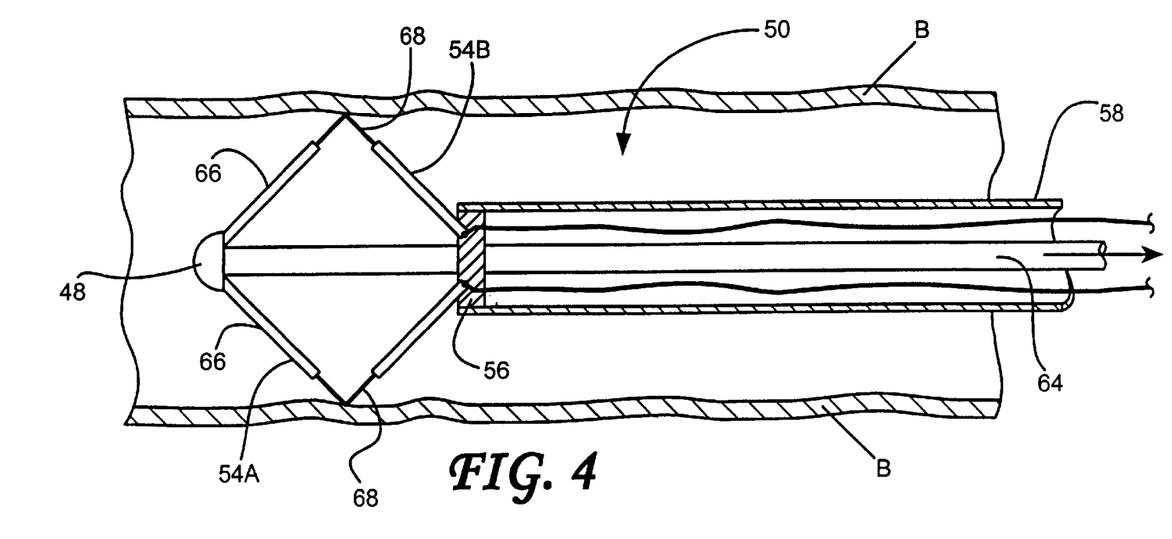
FIG. 4 is a side cross sectional view of the device of FIG. 3 in an enlarged state within a bronchial tube.

FIGS. 3 and 4 illustrate an alternative embodiment of a heat treatment apparatus 50. The heat treatment apparatus may be delivered to a treatment site in a collapsed configuration illustrated in FIG. 3. The heat treatment apparatus 50 includes two leaf spring or wire shaped electrodes 54A and 54B. The electrodes 54A, 54B are connected to an insulating end cap 56 of a hollow shaft 58. The electrodes 54A, 54B are electrically connected to the RF generator or other energy source by electric cables 60, 62. The heat treatment apparatus 50 is provided with a central shaft 64 which is slidable within the hollow shaft 58. The central shaft 64 has a shaft tip 48 which is connected to a distal end of each of the electrodes 54A, 54B.

Each of the electrodes 54A, 54B is preferably insulated with an insulating sleeve 66 except for an exposed contact section 68. The heat treatment apparatus 50 is delivered to the lumen of a bronchial tube to be treated either alone or through a catheter, bronchoscope, or other channel. The electrodes 54A, 54B are expanded radially outwardly by moving the central shaft 64 proximally with respect to the hollow shaft 58 of the heat treatment apparatus 50. Upon expansion, the exposed contact sections 68 of the electrodes 54A, 54B come into contact with the walls of the bronchial tube B, shown in FIG. 4. The electrodes 54A, 54B may be configured to bend at a predetermined location forming a sharp bend as shown in FIG. 4. Alternatively, the electrodes 54A, 54B may form a more gradual curve in the expanded configuration. The electrodes 54A, 54B are preferably connected to opposite poles of the energy source. Alternatively, both of the electrodes 54A, 54B may be connected to the same lead of the energy source and the external electrode 34 may be used. Upon completion of the treatment process the electrodes 54 are retracted back into the catheter for removal or moving to a subsequent treatment site.

Figure 5:
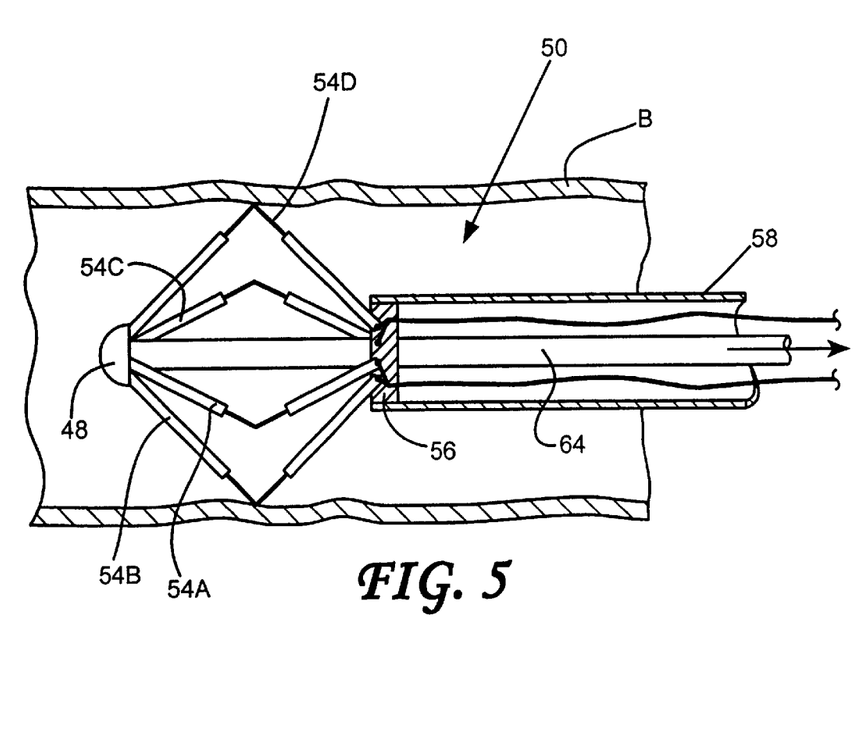
FIG. 5 is a side cross sectional view of an alternative embodiment of a heat treatment device with four electrodes in an enlarged state within a bronchial tube.
Figure 5A:
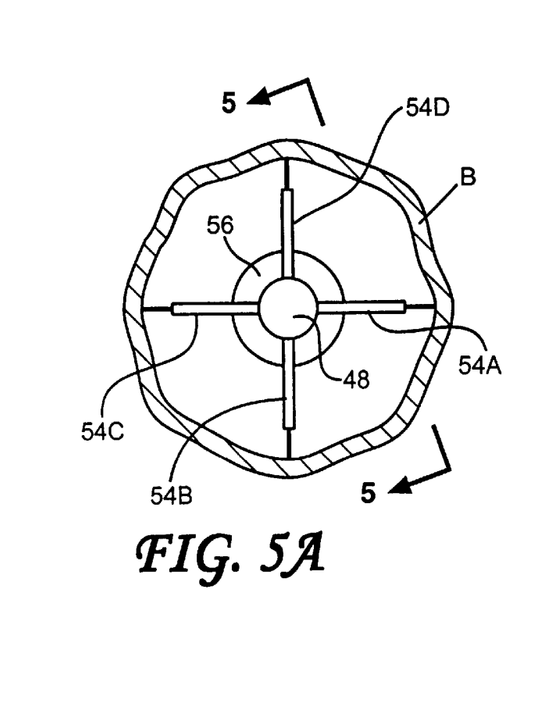
FIG. 5A is an end view of the device of FIG. 5.

FIGS. 5 and 5a illustrate an alternative embodiment of the invention in which the heat treatment apparatus 50 includes four electrodes 54A, 54B, 54C, 54D. The four electrode embodiment of FIGS. 5 and 5a operates in the same manner as the embodiments of FIGS. 3 and 4 with a slidable central shaft 64 employed to move the electrodes from a compressed configuration to the expanded configuration illustrated in FIGS. 5 and 5a. Each electrode 54A–54D is connected at a proximal end to the insulating end cap 56 of the hollow shaft 58 and at a distal end to the central shaft 64. Relative motion of the hollow shaft 58 with respect to the central shaft 64 moves the electrodes 54 from the collapsed to the expanded position.

Figure 6:
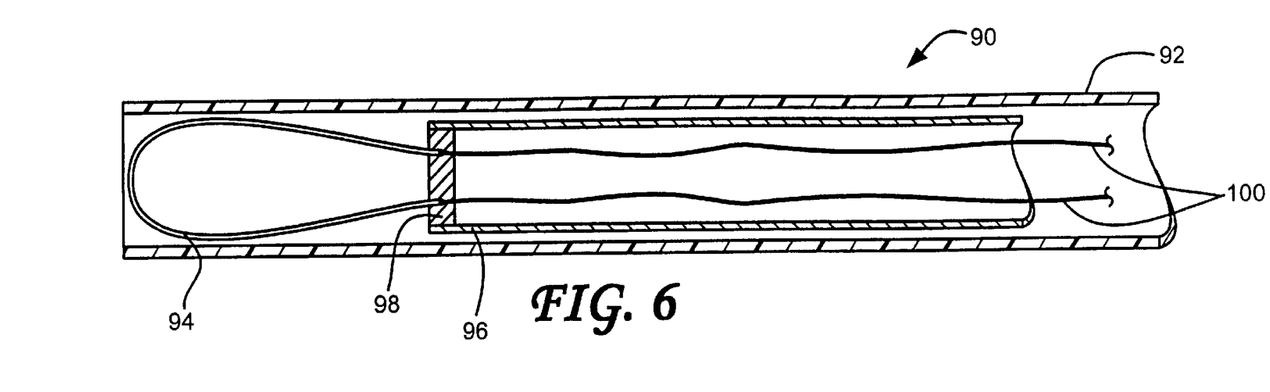
FIG. 6 is a side cross sectional view of an alternative embodiment of a heat treatment apparatus with a loop shaped electrode in a contracted state.
Figure 7:
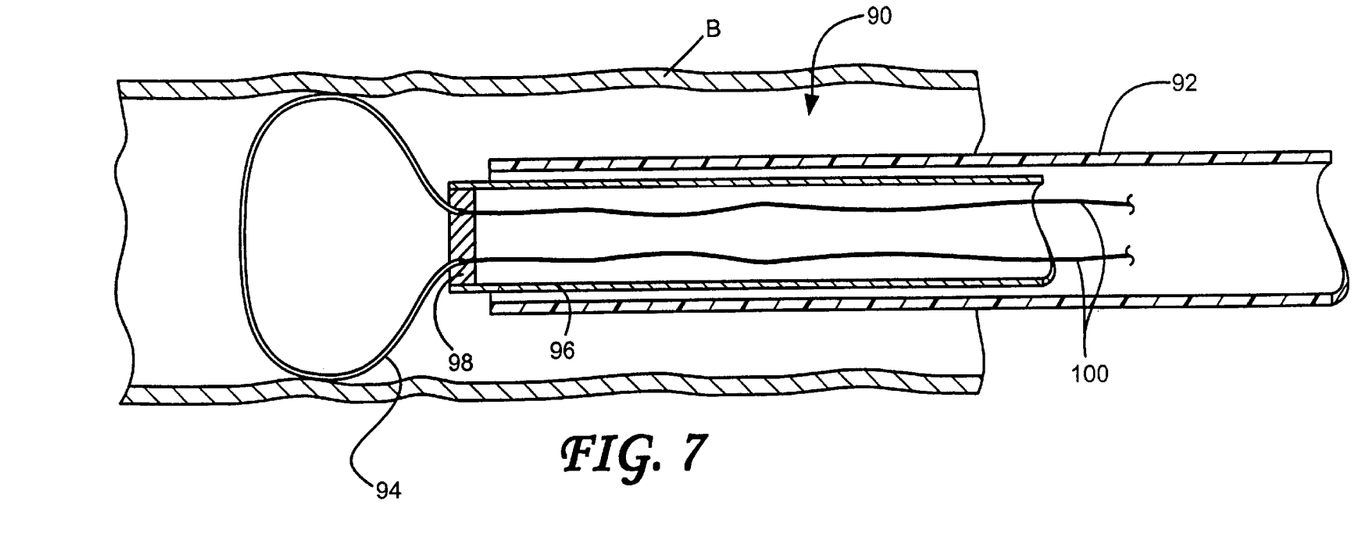
FIG. 7 is a side cross sectional view of the apparatus of FIG. 6 with the electrode in an expanded state within a bronchial tube.
Figure 8:
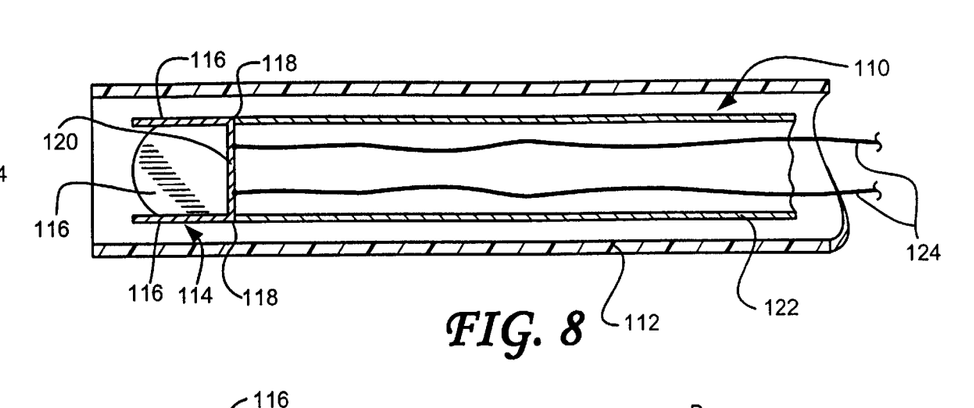
FIG. 8 is a side cross sectional view of an alternative embodiment of the invention with a plate shaped electrode in a contracted state.
Figure 9:
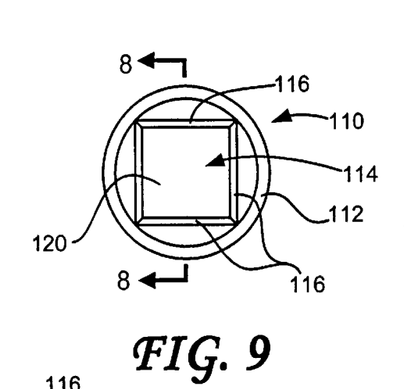
FIG. 9 is an end view of the apparatus of FIG. 8 in the contracted state.

FIGS. 6 and 7 illustrate a further embodiment of a heat treatment apparatus 90 employing one or more wire or leaf spring shaped loop electrodes 94. As in the previous embodiments, the loop electrode 94 expands from a contracted positioned within a catheter 92 as illustrated in FIG. 10 to an expanded position illustrated in FIG. 7. In the expanded position, the loop shaped electrode 94 comes into contact with the walls of the bronchial tube B. Although the embodiment of FIGS. 6 and 7 has been illustrated with a single loop shaped electrode 94, it should be understood that multiple loop shaped electrodes may also be use. The loop shaped electrode 92 is connected to the shaft 96 of the heat treatment apparatus 90 by an end cap 98 and is electrically connected to the energy source by the electric cables 100.

FIGS. 8–11 illustrate an alternative embodiment of a heat treatment apparatus 110 having a flexible plate shaped electrode 114. The flexible plate shaped electrode 114 is substantially flower shaped in plan having a plurality of petals or opposing portions 116 with curved distal ends extending from a central section 120. The petals 116 flex along a hinge line 118 to the compressed insertion configuration illustrated in FIG. 8 in which the petals 116 extend substantially perpendicularly from the central section 120 of the flexible plate shaped electrode 114.

Figure 10:
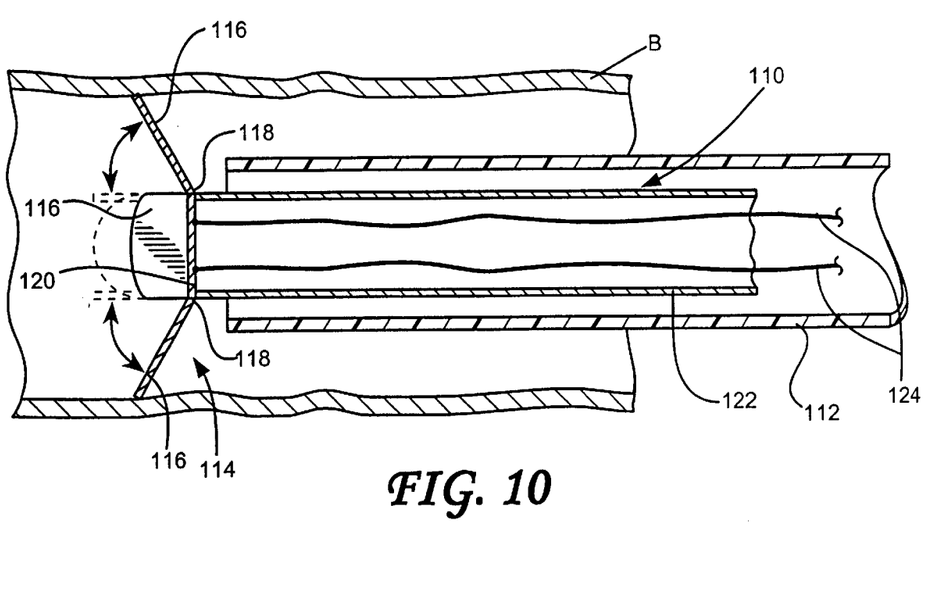
FIG. 10 is a side cross sectional view of the apparatus of FIG. 8 with the plate shaped electrodes in an expanded configuration.
Figure 11:
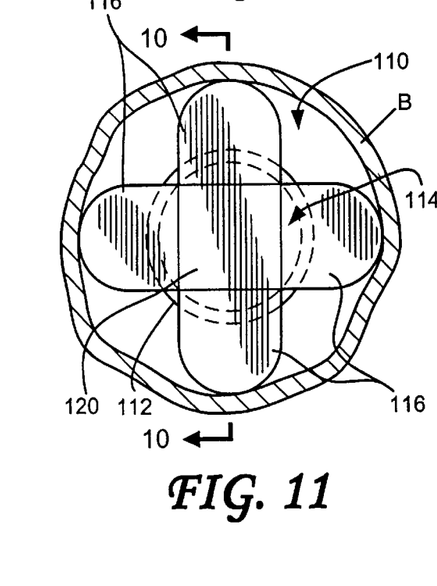
FIG. 11 is an end view of the expanded apparatus of FIG. 10.

As illustrated in FIG. 10 and 11, when the heat treatment apparatus 110 is moved distally with respect to the catheter 112 to deploy the electrode 114 the petals 116 move outwardly until the petal tips come into contact with the walls of the bronchial tube B. The flexible plate shaped electrode 114 is preferably formed of a conductive material and fixed to the end of a shaft 122. Electric cables 124 connect the plate shaped electrode 114 to the energy source.

The electrodes in each of the forgoing embodiments may be fabricated of any material which when compressed will return to an expanded configuration upon release of the compression forces. For example, one method of controlling the expansion of the electrodes is the use of shape memory alloy electrodes. With a shape memory alloy, the constraint of the electrodes within a catheter may not be necessary. The shape memory alloy electrodes may be formed to expand to an expanded energy delivery configuration upon heating to body temperature within the body. The expansion of the electrodes is limited by the size of the bronchial tube in which the electrode is positioned.

The heat treatment apparatus according to the present invention may be employed in a bipolar mode in which two different expandable electrodes are connected to two different outputs of the RF generator 18 having opposite polarities. For example, the electrodes 16A, 16B may be connected by the electrical cables 28, 30 to different terminals of the RF generator 18. Alternatively, when more than two electrodes 16 are employed, multiple electrodes may be connected to one terminal of the RF generator. In each of the embodiments of the heat treatment apparatus, the oppositely charged electrodes are separated by an insulating material. For example, in the embodiment of FIG. 1, the inner shaft 22 and outer shaft 24 are formed of an insulating material. Further, in the embodiments of FIGS. 3–5 the end cap 56 and central shaft distal tip 82 are formed of insulating materials.

In the case where the apparatus includes only one electrode 16 as shown in FIG. 2, the electrode will be connected to the positive or negative terminal of the RF generator 18 and the opposite terminal of the RF generator will be connected to the external electrode 32.

The frequency range of RF radiation useful in the present invention is typically about 10 KHz to about 100 MHz, preferably in the range of about 200 KHz to about 800 KHz. However, frequencies outside this range may be used at the discretion of the operating surgeon. Typically, the amount of power employed will be from about 0.01 to 100 watts and preferably in the range of about 1 to 25 watts for about 1 to 60 seconds. Alternatively, alternating current or microwave radiation typically in the frequency range of about 1,000 MHz to about 2,000 MHz and preferably from about 1,100 MHz to about 1,500 MHz may be used in place of RF radiation. In the latter case, the RF generator 18 is replaced with a microwave generator, and the electric cables 28, 30 are replaced with waveguides.

When the heat treatment apparatus with the bipolar electrodes is positioned inside the lumen of a bronchial tube, activation of the RF generator 18 causes tissue in the lumen wall to increase in temperature. The heating may be caused by resistance heating of the electrodes themselves and/or power losses through the tissue of the bronchial wall. The particular heat pattern in the tissue will depend on the path of the electric field created by the positioning and configuration of the electrodes.

In the monopolar mode, the external electrode 34, shown in FIG. 1, having a much larger surface area than the inner electrodes is placed on the outer surface of the patient's body. For example, the external electrode 34 can be an external metal mesh or a solid plate that is placed on the skin. Both the internal and external electrodes are connected to the RF generator 18 which produces an electric field at a high frequency. Because the collective surface area of the internal electrodes is much smaller than that of the outer electrode 34, the density of the high frequency electric field is much higher around the internal electrodes. The electric field reaches its highest density in the region near the internal electrodes. The increased density of the field around the internal electrodes produces localized heating of the tissue around the bronchial tube without causing significant heating of the body tissue between the bronchial tube and the external electrode.

In use, after the operating surgeon has placed the heat treatment apparatus within the lumen of a bronchial tube to be treated, if necessary, the catheter is retracted to expose the electrodes. In the case where the lumen of the bronchial tube has collapsed or is partially collapsed, the size of the energy emitting device is designed so that expansion of the electrodes causes the lumen to expand to its normal or non-collapsed diameter due to contact of the electrodes with the inner surface of the lumen. Alternatively, in the case where the lumen has not collapsed, the device is designed so that upon expansion the electrodes are in substantial contact with the inner surface of the lumen. Indeed, only minimum expansion may be necessary in treating a non-collapsed bronchial lumen.

The degree of expansion of the electrodes of the heat treatment apparatus can be monitored by means of endoscopy, fluoroscopy, or by other suitable imaging methods of the art. Generally, the heat required is induced in the tissue of the bronchial tube wall by the RF or microwave radiation emitting from the electrodes. The RF or microwave energy is applied while observing the tissue for changes via simultaneous endoscopy, or other suitable imaging methods of the art.

As is apparent, the inventive heat treatment apparatus can be employed to treat a bronchial tube regardless of whether the tube lumen has collapsed or not. Specifically, the devices can be used to treat bronchial tubes that have not collapsed, are partially collapsed, or are fully collapsed. Moreover, bronchial tubes may exhibit different degrees of closure depending on the state of respiration. For example, a bronchial tube may have a fully expanded lumen after inhalation but partially or completely closed during exhalation.

The electrodes employed in the present invention are constructed of a suitable current conducting metal or alloys such as, for example, copper, steel, platinum, and the like or of a plastic material with a conductive metal insert. The electrodes can also be constructed of a shape memory alloy which is capable of assuming a predetermined, i.e., programmed, shape upon reaching a predetermined, i.e., activation temperature. Such metals are well known in the art as described, for example, in U.S. Pat. Nos. 4,621,882 and 4,772,112 which are incorporated herein by reference. For the present invention, the shape memory metal used should have the characteristic of assuming a deflection away (i.e., expands) from the elongated rod when activated, i.e., heated in excess of the normal body temperature and preferably between 60° C. and 95° C. A preferred shape memory alloy is available as NITINOL from Raychem Corp., Menlo Park, Calif. In one embodiment, the electrodes are constructed of NITINOL in a predetermined shape and in the alloy's super elastic phase which can withstand very large deflections without deformation.

The function of the heat treatment apparatus is to apply a sufficient amount of energy to the walls of air passages to cause tissue in the walls to undergo a structural transformation to create more rigid walls that can support a non-collapsed, patent lumen. RF energy is no longer applied after there has been sufficient transformation, e.g., shrinkage, of the tissue fibers which may be gauged by removing the heating device from the treatment site and visually determining whether the lumen remains noncollapsed. Sufficient shrinkage may also be detected by fluoroscopy, external ultrasound scanning, pulse-echo ultrasound scanning, sensing the collapsing or straightening of the heating element with appropriate feedback variables, impedance monitoring or any other suitable method.

Substantial tissue transformation may be achieved very rapidly, depending upon the specific treatment conditions. Because the transformation can proceed at a rather rapid rate, the RF energy should be applied at low power levels. Preferably, the RF energy is applied for a length of time in the range of about 0.1 second to about 600 seconds, and preferably about 1 to about 60 seconds. Suitable RF power sources are commercially available and well known to those skilled in the art. In one embodiment the RF generator 18 employed has a single channel, delivering approximately 1 to 100 watts, preferably 1 to 25 watts, and most preferably 2 to 8 watts of RF energy and possessing continuous flow capability. The rate of collagen transformation can be controlled by varying the energy delivered to the heat treatment device. Regardless of the source of energy used during treatment, the lumen or the bronchial tube is maintained at a temperature of at least about 45° C., preferably between ° C. and 95° C. and more preferably between 70° C. and 85° C.

When the heat treatment apparatus includes multiple energy emitting devices, not all the electrodes need to be activated at the same time, that is, different combinations of electrodes can be employed sequentially. For example, in the case of the embodiment shown in FIG. 1, with two electrodes 16A, 16B, the electrodes can be activated simultaneously or sequentially.

In addition, when a heat treatment apparatus includes multiple energy emitting devices, the apparatus can operate in the monopolar, bipolar mode, or both modes at the same time. For instance, one of the electrodes can be designed to operate in the bipolar mode while another electrode operates in the monopolar mode.

When treating a person with obstructed air passages, a preliminary diagnosis is made to identify the air passages or bronchial tube that can be treated. In treating a particular site, excessive fluid is first removed from the obstructed air passage by conventional means such as with a suction catheter. Thereafter, the inventive heat treatment device is maneuvered to the treatment site. Depending on the diameter of the lumen of the bronchial tube, the device can be positioned directly at the treatment site or it can be positioned into place with a bronchoscope. The elongated shafts 22, 24 and outer catheter 12 are preferably made of a flexible material so that the catheter can be maneuvered through a bronchoscope. A bronchoscope is a modified catheter which includes an illuminating and visualization instrument for monitoring the treatment site and a channel for passing instruments (e.g., the treatment device) into the bronchial tubes.

In operation, the bronchoscope is advanced from the person's nasal or oral cavity, through the trachea, main stem bronchus, and into an obstructed air passage. The heat treatment apparatus is advanced forward through the bronchoscope to expose the tip of the heat treatment device before the treatment device is energized. Depending on the size of the treatment device, the treatment device can be moved to another position for further heat treatment of the air passage. This process can be repeated as many times as necessary to form a series of patency bands supporting an air passage. This procedure is applied to a sufficient number of air passages until the physician determines that he is finished. As is apparent, the procedure can be completed in one treatment or multiple treatments. After completion of the treatment, energy is discontinued and the treatment device is removed from the patient.

The heating apparatus can be made to provide protection against overheating of the connective tissue which will cause the collagen to denature. Temperature monitoring and impedance monitoring can be utilized in a system which provides feedback to the user in the form of sounds, lights, other displays or a mechanism which shuts down the application of energy from the heating element to the treatment site when sufficient tissue transformation is detected and to avoid burning of the treatment site. The amount of energy applied can be decreased or eliminated manually or automatically under certain conditions. For example, the temperature of the wall of the air passage, or of the heating element can be monitored and the energy being applied adjusted accordingly. The surgeon can, if desired, override the feedback control system. A microprocessor can be included and incorporated into the feedback control system to switch the power on and off, as well as to modulate the power. The microprocessor can serve as a controller to monitor the temperature and modulate the power.

The invention is also directed to the demonstration or instruction of the inventive surgical techniques including, but not limited to, written instructions, actual instructions involving patients, audio-visual presentations, animal demonstrations, and the like.

While the invention has been described in detail with reference to the preferred embodiments thereof, it will be apparent to one skilled in the art that various changes and modifications can be made and equivalents employed, without departing from the present invention.

What is claimed is:

1. A method of treating a bronchial tube comprising the steps of:
    advancing a treatment apparatus into the lumen of the bronchial tube wherein the apparatus comprises:
        at least one electrode which when energized causes tissue in a wall of the lumen to undergo a structural transformation effective to render the wall capable of supporting a non-collapsed lumen, wherein the at least one electrode is expandable radially outward to contact the wall of the bronchial tube; and
    activating the treatment apparatus to raise the temperature of the wall to sufficiently effect a structural transformation in the tissue of the wall.

2. The method of claim 1, wherein the wall is heated to a temperature of at least 45° C.

3. The method of claim 2, wherein the wall is heated to a temperature in the range between about 70° C. and about 85° C.

4. The method of claim 1, wherein the wall is heated for about 0.1 to about 600 seconds.

5. The method of claim 4, wherein the wall is heated for about 1 to about 60 seconds.

6. The method of claim 1, wherein the wall is heated by power losses through the tissue of the bronchial wall.

7. The method of claim 6, wherein the at least one electrode is energized by an alternating current at a radio frequency.

8. The method of claim 1, wherein the treatment apparatus is advanced into the lumen of the bronchial tube through the working channel of a steerable endoscope.

9. The method of claim 1, wherein the at least one electrode is resistively heated to treat the tissue of the bronchial wall.

10. The method of claim 9, wherein at least a portion of the treatment apparatus is insulated from surrounding tissue.

11. An apparatus for treating a wall of a bronchial tube comprising:
    a tubular member having a lumen;
    an elongated shaft having a distal portion, the elongated shaft is at least partially slidably positioned in the lumen of the tubular member;
    at least one electrode supported by the elongated shaft, which when energized causes tissue in the wall of the bronchial tube to undergo a structural transformation effective to render the wall capable of supporting the bronchial tube in a non-collapsed configuration;
    the at least one electrode having a proximal end attached to the tubular member and a distal end attached to the distal portion of the elongated shaft, and a contact section between the proximal and distal ends, wherein the contact section is configured such that proximal movement of the elongated shaft relative to the tubular member deflects the contact section of the electrode causing a sharp bend in the contact section and producing movement of the contact section in a radially outward direction from the elongated shaft towards the wall of the bronchial tube; and
    a source of energy electrically connected to the at least one electrode.

12. The apparatus of claim 11 wherein each electrode is biased to collapse the contact section radially inward towards the elongated shaft.

13. The apparatus of claim 11 wherein the source of energy produces energy that is selected from the group consisting of RF energy, alternating current, microwaves, and combinations thereof.

14. The apparatus of claim 11 wherein the at least one electrode comprises at least a first electrode and a second electrode, the first electrode is connected to a positive lead of a RF generator and the second electrode is connected to a negative lead of the RF generator.

15. The apparatus of claim 14 wherein the first electrode is electrically insulated from the second electrode.

16. The apparatus of claim 11 wherein the at least one electrode comprises at least four electrodes.

17. An apparatus for treating a wall of a bronchial tube comprising:
   a tubular member having a lumen;
   an elongated shaft having a distal portion, the elongated shaft is at least partially slidably positioned in the lumen of the tubular member;
   at least one electrode supported by the elongated shaft, which when energized causes tissue in the wall of the bronchial tube to undergo a structural transformation effective to render the wall capable of supporting the bronchial tube in a non-collapsed configuration;
   wherein each electrode comprises a plurality of opposing portions having a first end attached to the elongated shaft and a second free end, said electrode being expandable in a radially outward direction from the elongated shaft to assume an expanded shape; and
   wherein the tubular member restrains each electrode in a contracted shape wherein upon advancement out of the tubular member each electrode assumes the expanded shape causing the free end to contact the bronchial wall; and
   a source of energy electrically connected to the at least one electrode.

18. The apparatus of claim 17 wherein said plurality of opposing portions comprises at least one pair of opposing portions.

19. The apparatus of claim 17 wherein the at least one electrode comprises a plurality of electrodes each having substantially the same surface contour and each attached at spaced apart locations along a longitudinal axis of the elongated shaft.

20. The apparatus of claim 17 wherein the at least one electrode is spring biased to expand radially outward.

21. The apparatus of claim 17 wherein each electrode is formed of a shape memory material which causes the electrode to expand radially outwardly in response to a temperature change.

22. The apparatus of claim 17 wherein the source of energy produces energy that is selected from the group consisting of RF energy, alternating current, microwaves, and combinations thereof.

23. The apparatus of claim 17 wherein the at least one electrode comprises a first electrode and a second electrode, the first electrode is connected to a positive lead of a RF generator and the second electrode is connected to a negative lead of the RF generator.

24. The apparatus of claim 23 wherein the first electrode is electrically insulated from the second electrode.

25. The apparatus of claim 17 wherein the plurality of opposing portions comprises at least two curved sections which together form a conical shape, the at least two curved sections overlapping each other.

26. The apparatus of claim 25 wherein the at least two curved sections overlap each other further in the contracted shape than in the expanded shape.

27. The apparatus of claim 17 wherein the plurality of opposing portions comprises at least one pair of flexible plates located on substantially opposite sides of the elongated shaft.

28. The apparatus of claim 27 wherein the at least one pair of flexible plates comprises two pairs of flexible plates.

* * * * *